(12) United States Patent
Walter et al.

(10) Patent No.: US 7,599,465 B2
(45) Date of Patent: Oct. 6, 2009

(54) DETECTION OF THROMBI IN CT USING ENERGY DISCRIMINATION

(75) Inventors: Deborah Joy Walter, Terre Haute, IN (US); Yanfeng Du, Rexford, NY (US); Kelly Lynn Piacsek, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 150 days.

(21) Appl. No.: 11/692,086

(22) Filed: Mar. 27, 2007

(65) Prior Publication Data

US 2007/0189443 A1  Aug. 16, 2007

Related U.S. Application Data

(63) Continuation-in-part of application No. 10/904,630, filed on Nov. 19, 2004, now Pat. No. 7,209,536.

(51) Int. Cl.
*A61B 6/00* (2006.01)
(52) U.S. Cl. .......................................................... 378/4
(58) Field of Classification Search .................. 378/4, 378/9, 98.11
See application file for complete search history.

(56) References Cited

U.S. PATENT DOCUMENTS

| | | | | |
|---|---|---|---|---|
| 3,927,318 | A | * | 12/1975 | Macovski ...................... 378/6 |
| 5,400,378 | A | | 3/1995 | Toth |
| 5,485,492 | A | | 1/1996 | Pelc |
| 5,490,218 | A | * | 2/1996 | Krug et al. .................. 382/100 |
| 5,611,342 | A | | 3/1997 | Widder |
| 5,769,792 | A | * | 6/1998 | Palcic et al. ................. 600/477 |
| 5,987,094 | A | * | 11/1999 | Clarke et al. .................. 378/62 |
| 6,018,562 | A | * | 1/2000 | Willson .......................... 378/9 |
| 6,231,834 | B1 | | 5/2001 | Unger et al. |
| 6,285,740 | B1 | | 9/2001 | Seely et al. |
| 6,324,240 | B1 | * | 11/2001 | Yan et al. ........................ 378/4 |
| 6,343,111 | B1 | * | 1/2002 | Avinash et al. ........... 378/98.11 |
| 6,418,189 | B1 | | 7/2002 | Schafer |
| 6,480,565 | B1 | | 11/2002 | Ning |
| 6,671,540 | B1 | | 12/2003 | Hochman |
| 6,683,934 | B1 | * | 1/2004 | Zhao et al. ...................... 378/9 |
| 6,898,263 | B2 | * | 5/2005 | Avinash et al. .................. 378/4 |
| 6,904,118 | B2 | * | 6/2005 | Wu et al. ........................ 378/5 |
| 2002/0087071 | A1 | * | 7/2002 | Schmitz et al. ............. 600/420 |

(Continued)

OTHER PUBLICATIONS

Alvarez et al., Energy-selective Reconstructions in X-ray Computerized Tomography, Phys Med Biol, 1976, vol. 21, No. 5, pp. 733-744.*

(Continued)

*Primary Examiner*—Edward J Glick
*Assistant Examiner*—Alexander H Taningco
(74) *Attorney, Agent, or Firm*—Ziolkowski Patent Solutions Group, SC

(57) ABSTRACT

An imaging scanner includes a radiation source, a radiation detector, and a computer programmed to decompose CT data acquired by the radiation detector into a set of pixels, each pixel having at least a first basis material content and a second basis material content. The computer is further programmed to identify a first subset of the set of pixels as a possible embolism, based on the content of the first basis material and the content of the second basis material.

27 Claims, 9 Drawing Sheets

U.S. PATENT DOCUMENTS

| | | |
|---|---|---|
| 2002/0097320 A1 | 7/2002 | Zalis |
| 2003/0023163 A1 | 1/2003 | Johnson et al. |
| 2003/0113267 A1 | 6/2003 | Knopp et al. |
| 2003/0147502 A1 | 8/2003 | Heismann et al. |
| 2003/0152258 A1* | 8/2003 | Jabri et al. ............ 382/132 |
| 2003/0223627 A1 | 12/2003 | Yoshida et al. |
| 2004/0066881 A1* | 4/2004 | Reddy et al. ............ 378/5 |
| 2004/0101086 A1 | 5/2004 | Sabol et al. |
| 2004/0101088 A1* | 5/2004 | Sabol et al. ............ 378/4 |
| 2004/0101089 A1* | 5/2004 | Karau et al. ............ 378/4 |
| 2004/0101183 A1* | 5/2004 | Mullick et al. ............ 382/131 |
| 2004/0136491 A1* | 7/2004 | Iatrou et al. ............ 378/4 |
| 2004/0184574 A1 | 9/2004 | Wu et al. |
| 2004/0264627 A1 | 12/2004 | Besson |
| 2005/0018888 A1 | 1/2005 | Zonneveld |
| 2005/0084069 A1* | 4/2005 | Du et al. ............ 378/98.9 |
| 2006/0269043 A1* | 11/2006 | Heismann ............ 378/62 |

OTHER PUBLICATIONS

F. Rashid-Farrokhi et al., "Local Tomography in Fan-Beam Geometry Using Wavelets," 1996 IEEE, pp. 709-712.

S.B. Gokturk et al., "A Statistical 3-D Pattern Processing Method for Computer-Aided Detection of Polyps in CT Colonography," IEEE, vol. 20, No. 12, Dec. 2001, pp. 1251-1260.

J. Nappi et al., "Virtual Endoscopic Visualization of the Colon by Shape-Scale Signatures," IEEE, vol. 9, No. 1, Mar. 2005., pp. 120-131.

* cited by examiner

DETECTION OF THROMBI IN CT USING ENERGY DISCRIMINATION

CROSS-REFERENCE TO RELATED APPLICATION

The present application is a continuation in part of and claims priority of U.S. patent application Ser. No. 10/904,630 filed Nov. 19, 2004, the disclosure of which is incorporated herein.

BACKGROUND OF THE INVENTION

The present invention relates generally to radiographic imaging and, more particularly, to a method and system of detecting colon polyps in a colorectal region of a subject without cathartic preparation or insufflation of the colorectal region. The present invention also relates to a method and system of automatically detecting an embolism or thrombus in normal vascular tissue. The present invention is particularly applicable with photon counting and/or energy discriminating CT systems.

Colorectal cancer is a leading cause of cancer deaths. There are several accepted screening techniques that have been developed for the detection of potentially cancerous polyps. It is widely recognized that if these polyps can be detected and removed, the incidence and mortality rates of colorectal cancer may be reduced.

Furthermore, misdiagnosis often occurs in detecting abnormalities such as an embolism, a thrombus, or a blood clot in complicated blood vessel structures. Because of blockage in a blood vessel, vascular structure beyond the abnormality cannot receive contrast agent and may not be visible. If such abnormalities can be detected more efficiently, the incidence of misdiagnosis may be reduced.

Endoscopic colonoscopy is a common technique employed to detect potentially cancerous polyps. Colonoscopy, however, is an invasive and frequently uncomfortable experience for a patient. Recently, other techniques such as CT colonography, in which the principles of computed tomography is used to image the entire colon or colorectal region of a patient, have been developed and shown to be highly sensitive in the detection of these potentially cancerous polyps. While a CT colonography exam is considered much less invasive than a colonoscopy, CT colonography requires a cathartic bowel preparation, stool marker, and/or insufflation of the colon to capture contrast between polyps and stool in an image. While most patients do not experience complications from this cathartic preparation, the procedure can be highly disagreeable and is noted as a significant factor for patient non-compliance with screening regimens.

Furthermore, insufficient preparation can lead to fluid or stool retention which can obscure findings. As a result, it has been recommended that two exams be taken: one in the supine position and one in the prone position. Acquiring CT data when a patient is in the prone position allows for any residual fluid to collect at the bottom and allow a radiologist to uncover any polyps that may have been masked by the fluid when the patient was in the supine position. While taking two examines improves overall detection rates, it increases scan times and decreases patient throughput.

Recent advances in CT imaging include faster scanning speed, larger coverage, and higher power x-ray tubes. These improvements have enabled, for instance, the continuous scanning of the thorax in a single breath hold and continuous scanning of the vascular structure in the legs. These recent technological advances have improved the detection of pulmonary embolism (PE) and deep venous thrombus (DVT).

CT images may be enhanced by use of a contrast agent such as iodine to enhance the conspicuity of blood vessels in detecting PE and DVT. Using CT, the vascular structure can be distinguished from other tissue because of the high contrast between the contrast agent with respect to background tissue, which is mostly water. In some instances, though, the blood vessel can be blocked by an embolism, thrombus, or blood clot. Such blockage prevents the tissue beyond the blockage from receiving contrast agent, resulting in tissue beyond the thrombus that is not visible against the background tissue. In such cases, the radiologist must recognize anatomy within the image where the vascular structure is missing, and then must look for the cause of the blockage.

Because of the difficulty in determining a location of a thrombus, misdiagnosis can occur in identifying PE and DVT. As an example, in order to review the chest, a medical practitioner or radiologist may have to review 100-300 high resolution axial images, and the difficulty is exacerbated because over half of PE cases are diagnosed in an emergency situation.

It would therefore be desirable to design a CT system capable of imaging a colorectal region of a subject with contrast between polyps and stool without cathartic preparation or insufflation thereof. It would also be desirable to design an apparatus and method that quickly, easily, and automatically identifies possible PE and DVT in a CT image to a radiologist.

BRIEF DESCRIPTION OF THE INVENTION

The present invention is directed to a method and apparatus for CT embolism imaging that overcomes the aforementioned drawbacks. The present invention includes an imaging scanner having a radiation source, a radiation detector, and a computer programmed to decompose CT data acquired by the radiation detector into a set of pixels, each pixel having at least a first basis material content and a second basis material content, and identify a first subset of the set of pixels as a possible embolism, based on the content of the first basis material and the content of the second basis material.

The present invention is applicable with a photon counting (PC) radiographic system having a radiation energy detector configured to detect radiation energy at a given flux rate and output signals indicative of the detected radiation energy. A shaper unit with a given shaping time is connected to receive the electrical signals and conditions them to provide electrical pulses indicative of the radiation photon energy. A PC channel is connected to receive the electrical signals and sample the electrical pulse signals of a certain height or intensity indicative of the photon energy by an adjustable pulse height discriminator or threshold. The PC channel is further configured to provide a photon count output over a sampling interval. The system also includes a control operationally connected to the PC channel and configured to automatically adjust the shaping time at least as a function of the given flux rate. The system also includes a control operationally connected to the PC channel and configured to automatically adjust the sensitivity to pulse height or threshold discriminator as a function of the given flux rate or shaping time.

The present invention is also applicable with an integrating energy selective detector, where the received radiation is registered in two or more energy ranges that may overlap through the use of either direct or indirect conversion detector materials using a layered design or depth of interaction to differentiate the energy bins.

The present invention is also applicable with an energy integration detector and an x-ray source modulated to adjust the spectra for two or more different energy functions.

Therefore, in accordance with one aspect of the present invention, an imaging scanner is disclosed and includes a radiation source, a radiation detector, and a computer programmed to decompose CT data acquired by the radiation detector into a set of pixels, each pixel having at least a first basis material content and a second basis material content. The computer is further programmed to identify a first subset of the set of pixels as a possible embolism, based on the content of the first basis material and the content of the second basis material.

In accordance with another aspect of the present invention, a method of CT imaging includes acquiring energy sensitive CT data from an ROI of a subject, classifying the acquired energy sensitive CT data as pixels having content from a first basis material and content from a second basis material, and determining a first set of the classified pixels as a possible blood clot.

In accordance with yet another aspect of the present invention a computer program is stored on a computer readable storage medium. The computer program includes receiving energy sensitive CT data acquired from a subject decompose the energy sensitive CT data into at least two basis material datasets, assigning a first basis material content and a second basis material content to each pixel of an image, identifying a first set of pixels in the image as possible blood clot based on the first and second basis material content, and reconstructing a conventional CT image with the first set of pixels highlighted.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the Drawings.

DETAILED DESCRIPTION OF THE PREFERRED EMBODIMENT

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other radiation energy sources.

Figure 1:
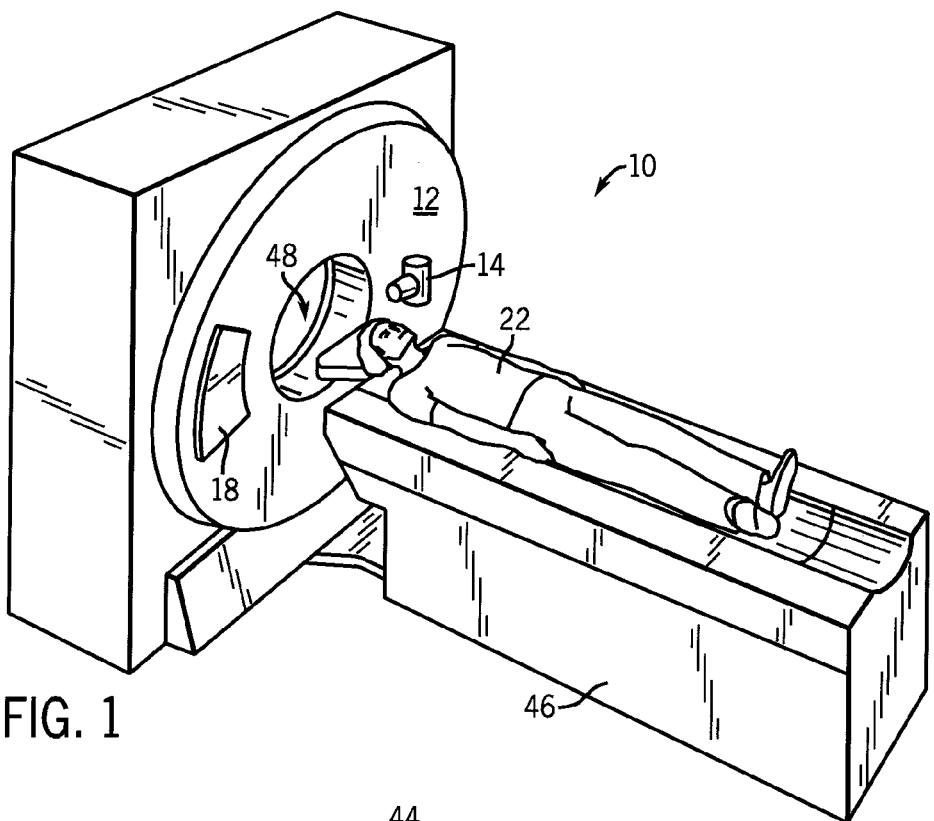
FIG. 1 is a pictorial view of a CT imaging system.
Figure 2:
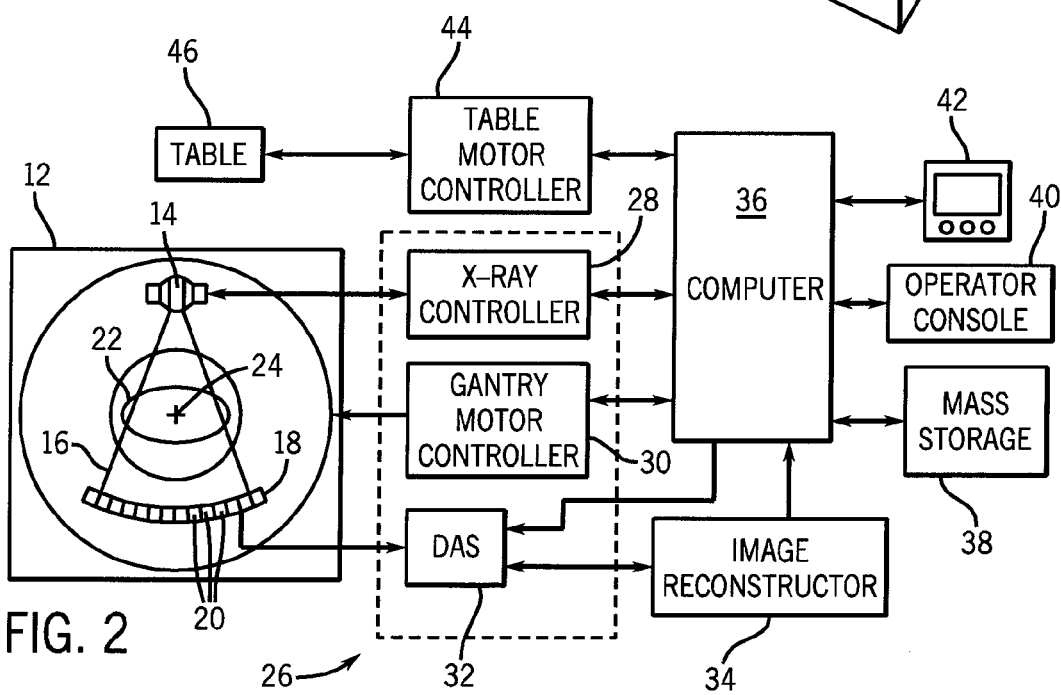
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly 18 on the opposite side of the gantry 12. Detector assembly 18 is formed by a plurality of detectors 20 which together sense the projected x-rays that pass through a medical patient 22. Each detector 20 produces an electrical signal that represents not only the intensity of an impinging x-ray beam but is also capable of providing photon or x-ray count data and energy level, and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 reviews data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated display screen 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

In one embodiment, CT system 10 is an energy-discriminating computed tomography (EDCT) system and is configured to be responsive to different incident x-ray spectra. This can be accomplished by acquiring projection data sequentially using different x-ray tube voltages. For example, two scans are acquired either back to back or interleaved in which the tube operates at 80 kVp and 160 kVp potentials, for example, generating a low and high energy spectrum respectively. Alternatively, special filters are placed between x-ray source 14 and the subject 22 such that detector rows collect projections of different x-ray energy spectrum either sequentially or interleaved. Yet another embodiment is to use energy sensitive photon counting detectors such that each x-ray photon reaching the detector is recorded with its photon energy. Yet another embodiment is to use energy sensitive detectors such that direct or indirect conversion material is used to separate photons into two or more energy bins that may overlap through the use of detector layers or depth of interaction detectors.

EDCT can lessen or eliminate problems, such as lack of energy discrimination or material characterization, associated with some CT systems altogether. In the absence of object scatter, EDCT system 10 may be used to separately detect two regions of the incident photon energy spectrum, the low energy and the high energy portions of the incident x-ray spectrum. The behavior at any other energy can be derived based on the signal from the two energy regions. This phenomenon is driven by the fundamental fact that in the energy region where CT is interested, two physical processes dominate the x-ray attenuation: (1) Compton scatter and (2) the Photoelectric effect. In order to characterize the behavior of an object causing attenuation of the x-ray beam, two independent parameters are measured. Thus, detected signals from the two energy regions provide sufficient information to resolve the energy dependence of the object being imaged; hence, the composition of the material can be characterized.

The data analysis used in EDCT includes Compton and photoelectric decomposition and/or Basis Material Decomposition (BMD). In Compton and photoelectric decomposition, a pair of images is generated, which separately presents the attenuation from the Compton and photoelectric processes—instead of obtaining one image characterizing the overall attenuation coefficient in the reconstructed CT image. Also, a slight modification in the processing allows the generation of images representing density and effective atomic number. The BMD method is based on the concept that the x-ray attenuation of any given material in the energy range can be represented by a linear combination of a density mixture of two known materials. These two materials are called the Basis Materials. Using BMD, two reconstructed images are obtained, each image representing the equivalent density of one of the basis materials. Since density is independent of x-ray photon energy, these images are relatively free of beam hardening artifacts. Additionally, the Basis Material is chosen to target a material of interest, thus enhancing the image contrast.

It should be noted that in order to optimize a multi-energy CT system not implementing energy discrimination with photon counting, the larger the energy separation in the x-ray spectra, the better the image quality. Also, the photon statistics in these two energy regions should be comparable, otherwise the energy region with reduced statistical information will dominate the noise in the reconstructed image.

There are different methods to obtain dual energy measurements: (1) scan with two distinctive energy spectra, (2) detect photon energy according to penetration depth at the detector, or (3) photon counting with energy discrimination. Photon counting provides clean spectra separation and an adjustable energy separation threshold for balancing photon statistics.

While applicable with each of the aforementioned methods, the present invention will be further described with respect to a multi-energy system having energy discriminating radiation detectors capable of counting photon events and associating an energy level to a counted event. To combat saturation of these detectors, a number of saturation techniques may be used. One such technique is described below.

Generally, high-sensitivity photon counting radiation detectors are constructed to have a relatively low dynamic range. This is generally considered acceptable for photon counting detector applications since high flux conditions typically do not occur. In CT detector designs, low flux detector readings through the subject are typically accompanied by areas of high irradiation in air, and/or within the contours of the scan subject requiring CT detectors to have very large dynamic range responses. Moreover, the exact measurement of photons in these high-flux regions is less critical than that for low-flux areas where each photon contributes an integral part to the total collected photon statistics. Notwithstanding that the higher flux areas may be of less clinical or diagnostic value, images reconstructed with over-ranging or saturated detector channel data can be prone to artifacts. As such, the handling of high-flux conditions is also important.

An x-ray flux management control is designed to prevent saturation of PC x-ray systems having detector channels characterized by low dynamic range. Dynamic range of a detector channel defines the range of x-ray flux levels that the detector channel can handle to provide meaningful data at the low-flux end and not experience over-ranging or saturating at the high flux end. Notwithstanding the need to prevent over-ranging and to provide diagnostically valuable data, the handling of low-flux conditions, which commonly occur during imaging through thicker cross-sections and other areas of limited x-ray transmission, is also critical in detector design. As such, the x-ray flux management control described herein is designed to satisfy both high flux and low flux conditions.

Generally, operation of a photon counting detector is characterized by a shaping time curve that is fixed. The shaping time curve defines a relationship or balance between charge integration time (single-event signal level) and detector channel recovery time so as to provide acceptable PC count-rates, noise suppression, and energy resolution. Typically, the detector channel is constructed to have a shaping time that favors low-flux rate conditions. That is, for low-flux rate conditions, which translate to fewer x-ray photons, a longer shaping time is preferred so that the entire photon charge cloud is integrated and SNR is optimized. There is generally relatively little constraint on the time necessary to integrate the entire photon cloud. Since the condition is characterized by low-flux, the detector channel is not likely to saturate while integrating or otherwise sampling the entire photon cloud. On the other hand, the low-flux rate favored, fixed time shaping may be insufficient for high-flux rate conditions. Moreover, if the time shaping is fixed to match or correspond to high-flux rate conditions, a negative impact on SNR and energy resolution during low-flux rate conditions follows.

Figure 3:
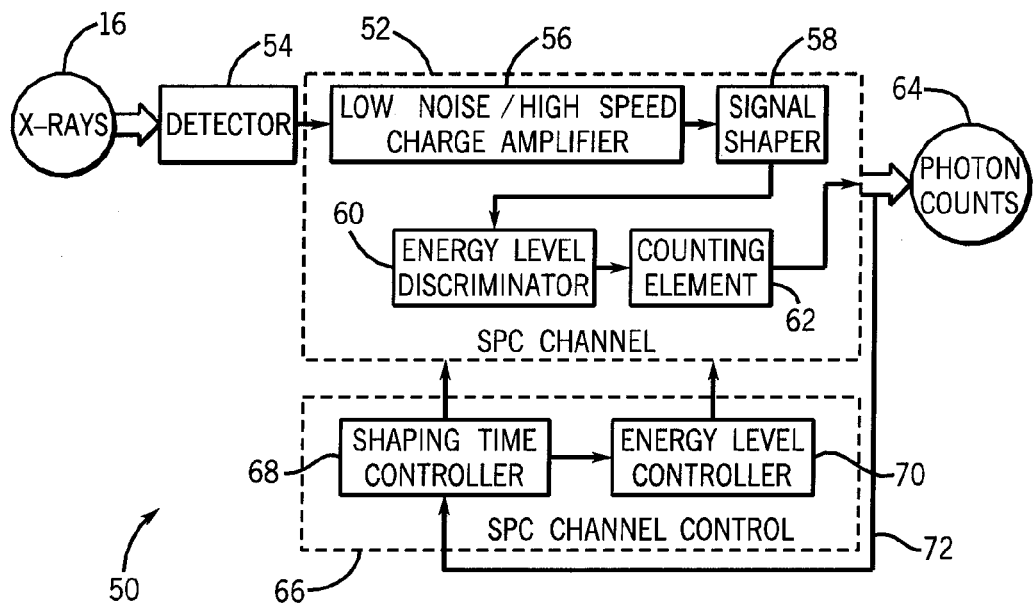
FIG. 3 is a block schematic diagram of a detector assembly according to the present invention.

Accordingly, the CT system is designed to dynamically and automatically control the shaping time of a detector channel such that low-flux as well as high-flux rate conditions are optimally addressed. Referring now to FIG. 3, a block schematic diagram of an x-ray detection system 50 applicable with the present invention is shown. System 50 includes a PC channel 52 connected to receive electrical signals from a detector element 54. Detector 54 is constructed to detect x-rays 16 projected by an x-ray source and attenuated by a subject, such as a medical patient. It is understood that the present invention is applicable with gamma rays and other forms of radiographic energy.

PC channel 52 includes a low-noise/high-speed charge amplifier 56 connected to receive the electrical signals from detector element 54. The amplified output of amplifier 56 is then input to a signal shaper 58 constructed to extract individual photon events from the electrical signals. Energy level discriminator 60 is connected to signal shaper 58 and is designed to filter photons based on their pulse height energy level relative to one or more thresholds. To this end, those photons having energy levels outside a desired range are excluded from counting and processing for image reconstruction. Minimally, discriminator 60 is designed to exclude those photons having an energy level corresponding to noise in the system. It is contemplated that multiple thresholds may be used to define energy level ranges. Counting element 62 receives those photons not filtered out by energy level discriminator 60 and is constructed to count the number of photons received at the detector and provide a corresponding output 64. As will be described and in contrast to known PC channels, operation PC channel 52 is governed by a variable shaping time.

PC channel 52 is operationally connected to a control 66 that includes a shaping time controller 68 and, preferably, an energy level controller 70. While it is preferred that control 66 include energy level controller 70, it is contemplated that the present invention may be carried out without it. In one embodiment, PC channel 52 includes an active filter whose operation defines the channel's shaping time. In this regard, resistive and capacitive characteristics of the active filter can be adjusted to manipulate the channel's shaping time properties.

Shaping time controller 68 is connected to PC channel 52 and is designed to adjust the shaping time characteristics of PC channel 52 based on photon count feedback received across feedback loop 72. More particularly, shaping time controller 68 increases the channel's shaping time when the detector element is exposed to low x-ray flux as measured by the number of photons counted 64. In contrast, when the x-ray flux on the detector element 54 increases, the time shaping controller decreases the time shaping or sampling window of PC channel 52.

As such, when the detector is experiencing higher x-ray flux, the amount of time the PC channel spends sampling the photon charge cloud is reduced. Accordingly, less precise photon and energy discriminatory data with respect to the photon charge cloud is determined; however, the channel recovers at a rate sufficient to avoid over-ranging. In this regard, as the shaping time or sampling window is caused to decrease, more photons are inspected for data, i.e. counted, while each detected photon provides less precise energy discriminatory information. And, under high flux conditions, each individual photon assumes less importance and the overall system performance and image quality is minimally impacted by the reduced SNR. On the other hand, when the detector is experiencing lower x-ray flux, the amount of time the PC channel spends to sample the photon charge cloud is lengthened which allows sufficient time to sample the entire photon charge cloud and attain relatively precise photon count and energy discriminatory data.

As referenced above, control 66 includes, in one embodiment, an energy level controller 70. Since the measured photon signal levels vary with channel shaping time, automatic energy discriminator energy level controller 70 is coupled to shaping time controller 68 and PC channel 52 to adjust or otherwise calibrate the energy level threshold of the PC channel in response to an adjustment in the shaping time. By performing appropriate channel calibration, photons having an acceptable or decreased energy level are counted to assure linear energy response independent of channel shaping time and count rate.

Figure 4:
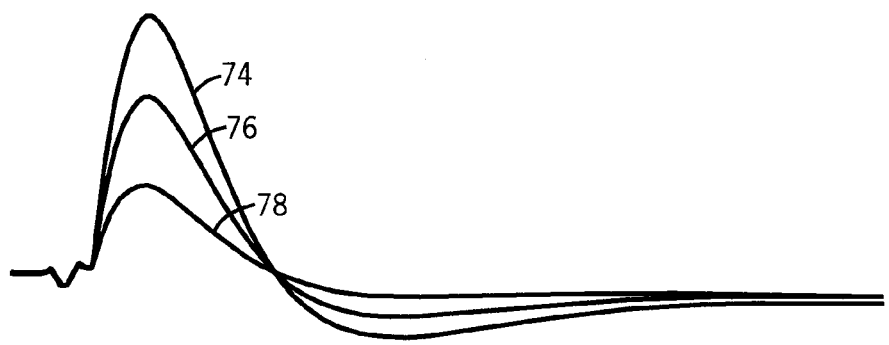
FIG. 4 is a graph illustrating signal amplitude plots for a number of shaping times for an exemplary PC detector.

Referring now to FIG. 4, a number of amplitude plots for several shaping time curves for an exemplary PC channel are illustrated. Decreasing the shaping time increases the potential count rate but, as shown, decreases the signal amplitude and increases noise. Specifically, adjusting the time shaping defined by curve 74 to that defined by curve 76 increases the potential count rate, but causes an inversely related decline in collective signal strength of the counted photons and negatively affects SNR. A further decrease in shaping time, i.e. curve 76 to curve 78 results in a further increase in count rate potential, but with additional decline in signal strength and SNR.

The present invention is further directed to CT colonography with the capturing of contrast between polyps and stool in a colorectal region of a patient using energy-discriminating CT data acquired with a CT system such as that described with respect to FIGS. 1-4. As described above, it is critical to prevent saturation or over-ranging of energy discriminating detectors at high x-ray flux conditions such that the output of a given radiation detector may be used for image reconstruction. Heretofore, a variable shaping time controller has been described to prevent over-ranging of a radiation detector. However, it is contemplated that the present invention is applicable with CT systems incorporating other techniques and mechanisms to prevent over-ranging of radiation detectors under high flux conditions including, but not limited to, dynamic collimation, dynamic two-current control, and variable shaped bowtie filters. In this regard, the energy sensitive or discriminating CT data avoids the inherent uncertainty of CT data acquired with a conventional CT system. That is, it is well known that different materials or mixtures of materials having different attenuation properties can produce the same CT or Hounsfield number if the density values are different such that the product of attenuation and density in the differing materials are equal. That is, the CT number for a given image voxel is a function of the number of photons impinged upon the radiation detector as well as the energy level of the x-rays received.

In contrast, the CT system described herein is capable of counting the number of photons received as well as determining an energy level for each received or counted photon. As will be described in greater detail below, it is possible from the photon count as well as the energy level of a counted photon to determine not only the density of an imaged material as well as the type of material imaged. This information can then be used to distinguish between stool and polyps or between contrast agent such as an intravenously administered Iodine and/or orally administered Barium Sulfate agent, and other tissues of similar CT number characteristics. One skilled in the art will appreciate that intravenous Iodine goes to the polyps or the colon wall whereas orally administered Barium Sulfate goes to the stool. The present invention is applicable with each and may be used to distinguish between unenhanced tissues and contrast enhanced tissues. Further, the present invention may be used to distinguish between different contrast agents delivered to different sites or tissues.

Figure 5:
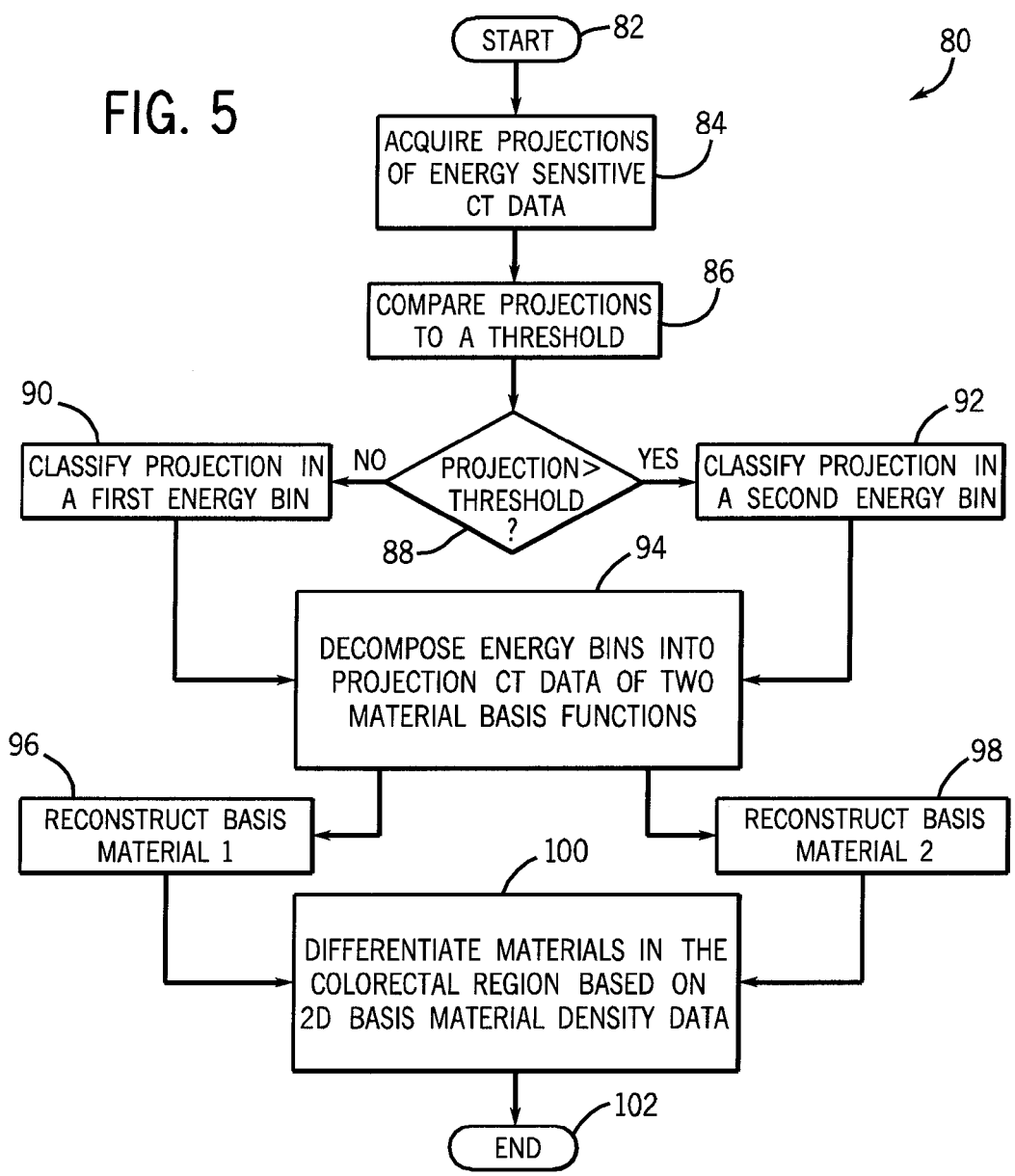
FIG. 5 is a flowchart setting forth steps of a CT colonography exam according to the present invention.

Referring now to FIG. 5, the steps of a colonography imaging process in accordance with one embodiment of the present invention will be described. The process 80 begins at 82 with the prescription of a CT exam to acquire CT data from a colorectal region of a patient. A CT scan is then administered at 84 consistent with the parameters established at 82 to acquire projections of energy sensitive CT data. As described above, energy sensitive CT data includes photon count as well as energy level information. As the acquired CT data includes photon counts as well as energy level information, the present invention contemplates a comparison of a projection to a threshold at 86 so as to bin the projection data into one or more energy bins. As such, projection is compared to a threshold at 88. Depending upon where the projection falls with respect to the threshold, the projection will be classified in either a first energy bin 90 or a second energy bin 92. While only two energy bins are illustrated in FIG. 5, it is contemplated that more than two energy bins or classifications may be applied in decomposing the energy sensitive CT data. It is also contemplated, as described above, that two or more energy bins may be acquired through other mechanisms, such as the use of modulating the energy spectra of the x-ray tube either through the adjustment of the peak voltage (kVp) or through the use of special filter materials.

Once the energy bins are computed, the energy bins are decomposed into projection CT data representing two basis materials 94. The two projection data sets are processed to form a reconstructed image of the density value of the first material 96 and a second material 98. It is contemplated that in lieu of decomposing the energy bins into two basis materials, the energy bins can be decomposed into another set of orthogonal basis functions, such as: effective atomic number and density, or photoelectric and Compton scattering components. Once the basis material density values are available, the two dimensional information can be used to differentiate the materials found in the colorectal region base on the two dimensional basis material density data 100. The two dimensional data has more information than the one dimensional data that is available from a conventional CT processing technique. Furthermore, the decomposition technique can separate materials that have the same CT number but a different representation in the basis material two-dimensional map due to different chemical compositions. In, this regard, more contrast between materials is generated using the material basis decomposition. The process is then completed at 102 with displaying of the image for evaluation by a radiologist or other health care provider. The display of the image can include additional post-processing of the data to generate a color-coded image that highlights materials of specific chemical compositions.

In the example illustrated above, the energy bins are designed to segment data corresponding to water from data corresponding to orally administered contrast agent. In this regard, the corresponding projections will be reconstructed to form images that represent the density of the contrast agent administered as well as the density of the water present in the image. As such, areas in the image that are infused with contrast agent will be differentiated from normal tissue more easily than relying on CT number density alone. Further, different tissues can be classified and separated, and ultimately differentially weighted such that tissue differentiation within the image is more readily ascertainable even though the CT number associated with the tissues and/or contrast agent is equal. In this regard, each pixel in a reconstructed image may be encoded with a value that during image reconstruction is used to differentiate that imaged in a given pixel from that imaged in another pixel. It is also contemplated that rather than a composite image, an image of only colon polyps may be reconstructed. That is, based on the tissue differentials consistent with the photon count and energy discriminating data, data corresponding to colon polyps can be isolated and used for image reconstruction while all non-polyp data is set to a background level.

Figure 6:
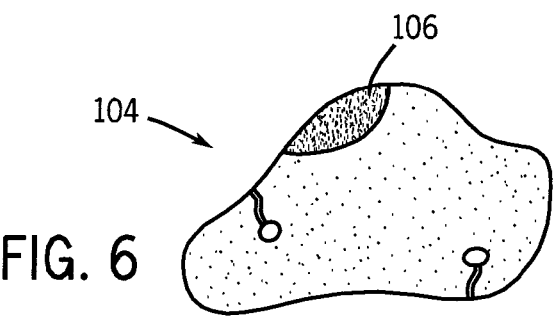
FIG. 6 is a schematic view of a colorectal region of a subject having polyps disposed therein.

Referring now to FIG. 6, a colorectal region of a subject is schematically illustrated as including a polyp 106 surrounded by stool 108 in the colorectal region 104. In a preferred embodiment, the colorectal region is not insufflated or subjected to cathartic preparation prior to CT data acquisition. It is contemplated, however, that a contrast agent such as an intravenously administered Iodine or orally administered Barium Sulfate may be used to further capture contrast between colon polyps that may be potentially cancerous from normal tissue within the colorectal region. As is well known, a contrast agent may be selected that is easily absorbed by cancerous cells but not other tissues within the colorectal region. As such, cancerous or other pathological abnormalities within the colorectal region may develop pools of contrast agent that can be used to identify a potentially cancerous colon polyp. In this regard, through the acquisition and decomposing of energy sensitive and/or energy discriminating CT data, it is possible to identify, automatically, a malignant polyp within the colorectal region. That is, the material basis density values can indicate that contrast agent targeted to cancerous cells is present in the polyp as opposed to naturally occurring tissue that may have similar CT number. For example, the material basis values may be compared to a lookup table of empirical data and based on that comparison can be identified as a colon polyp or stool. Additionally, by comparing material density values to a neighboring values in a reconstructed image, it is possible to determine the size as well as shape of an identified or detected colon polyp. In this regard, it is possible to implement detection processes to use the CT number, shape, texture, and material composition of a selected portion of a reconstructed image to automatically detect and characterize colon polyps.

The present invention is further directed to the capturing of contrast between an embolism and a vasculature of a patient using energy-discriminating CT data acquired with a CT system such as that described with respect to FIGS. 1-4. As described above, areas in an image that are infused with contrast agent may be differentiated from normal tissue more easily than relying on CT number density alone. For example, a blood vessel and an embolism, such as a thrombus or blood clot may be differentially weighted within the image even though the CT number associated with them may be equal. In this regard, each pixel in a reconstructed image may be encoded with a value that is used to automatically differentiate that imaged therein from that imaged in another pixel during image reconstruction. It is also contemplated that, rather than displaying normal and contrast-enhanced tissues, an image highlighting only an embolism may be reconstructed. That is, based on the tissue differentials consistent with the photon count and energy discriminating data, data corresponding to an embolism may be isolated and used for image reconstruction while non-embolism data is set to a background level.

Figure 7:
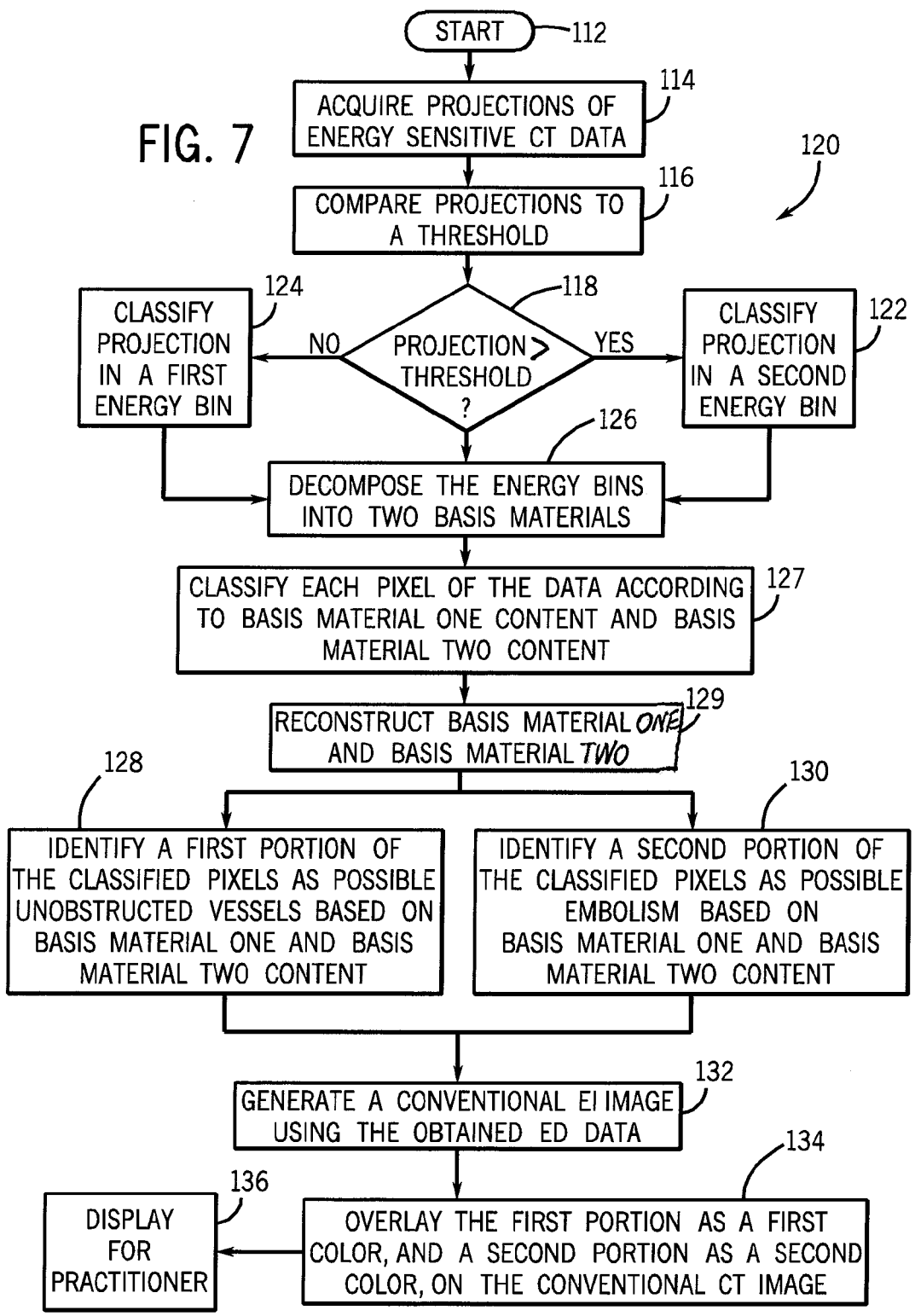
FIG. 7 is a flow diagram according to an embodiment of the present invention.

Referring now to FIG. 7, an embolism imaging process 120 in accordance with one embodiment of the present invention is shown. The process 120 begins at 112 with the prescription of a CT exam to acquire CT data from a designated region of a patient. A CT scan is then administered at 114 consistent with the parameters established at 112 to acquire projections of energy sensitive CT data. As described above and with respect to FIG. 5, energy sensitive CT data includes photon count as well as energy level information. As the acquired CT data includes photon counts as well as energy level information, the present invention contemplates a comparison of a projection to a threshold at 116 so as to bin the projection data into one or more energy bins. As such, process 120 determines whether the projection is greater than the threshold at 118. Depending upon where the projection falls with respect to the threshold, the projection will be classified in either a first energy bin 124 or a second energy bin 122. For example, if the projection is less than or equal to the threshold, the protection is classified in the first energy bin at 124. If the projection is greater than the threshold, the protection is classified in the second energy bin at 122, While only two energy bins are illustrated in FIG. 7, it is contemplated that more than two energy bins or classifications may be applied in decomposing the energy sensitive CT data. It is also contemplated, as described above, that two or more energy bins may be acquired through other mechanisms, such as the use of modulating the energy spectra of the x-ray tube either through the adjustment of the peak voltage (kVp) or through the use of special filter materials.

Still referring to FIG. 7, once the projections have been classified at 122 and 124, the energy bins are decomposed into two basis material bins at 126. It is contemplated that in lieu of decomposing the energy bins into densities, the energy bins can be decomposed into another set of orthogonal basis functions, such as: effective atomic number and density, or photoelectric and Compton scattering components. The two projection data sets may be processed to classify the content, for instance, the density, of the first basis material and the second basis material at 127. Once the basis material density values are available, the two dimensional information can be used to differentiate the materials based on the two dimensional basis material density data 127. Basis material one and basis material two are reconstructed at 129. The two dimensional data has more information than the one dimensional data that is available from a conventional CT processing technique. Furthermore, the decomposition technique can separate materials that have the same CT number but a different representation in the basis material two-dimensional map due to different chemical compositions. In, this regard, contrast between materials is generated using the material basis decomposition.

Based on the content of the two basis materials, pixels may be identified as possible unobstructed blood vessels at 128, and pixels may be identified as possible thrombus, embolism, or blood clot at 130. Using the ED data obtained, a conventional CT image is generated at 132. At step 134, pixels identified in either step 128 or step 130 are overlaid over the conventional CT image generated at step 132. Preferably, identified pixels of possible unobstructed blood vessels are displayed using a first color or identifier, and identified pixels of possible thrombus, embolism, or blood clot are displayed as a second color or identifier. In a preferred embodiment, the identified pixels are overlaid over the conventional CT image in an image layer separate from the image layer containing the conventional CT image pixels. In this manner, a medical practitioner or radiologist may toggle the image layer containing the identified pixels between a visible and a hidden mode to allow unobstructed viewing of the conventional CT image if so desired. Alternatively, pixels of the conventional CT image may be replaced with highlighting pixels such that the highlighted pixels are integrated with the conventional CT image. The conventional CT image with color overlay is automatically displayed for a radiologist or practitioner at step 136. The display of the image can include additional post-processing of the data to generate a color-coded image that highlights materials of specific chemical compositions.

In the example illustrated above, the energy bins are designed to segment data corresponding to water from data corresponding to injected contrast agent. In this regard, the corresponding projections will be reconstructed to form images that represent the density of the contrast agent administered as well as the density of the water present in the image. As such, areas in the image that are infused with contrast agent will be differentiated from normal tissue more easily than relying on CT number density alone. Further, different tissues can be classified and separated, and ultimately differentially weighted such that tissue differentiation within the image is more readily ascertainable even though the CT number associated with the tissues and/or contrast agent is equal. In this regard, each pixel in a reconstructed image may be encoded with a value that during image reconstruction is used to differentiate that imaged in a given pixel from that imaged in another pixel.

Figure 8:
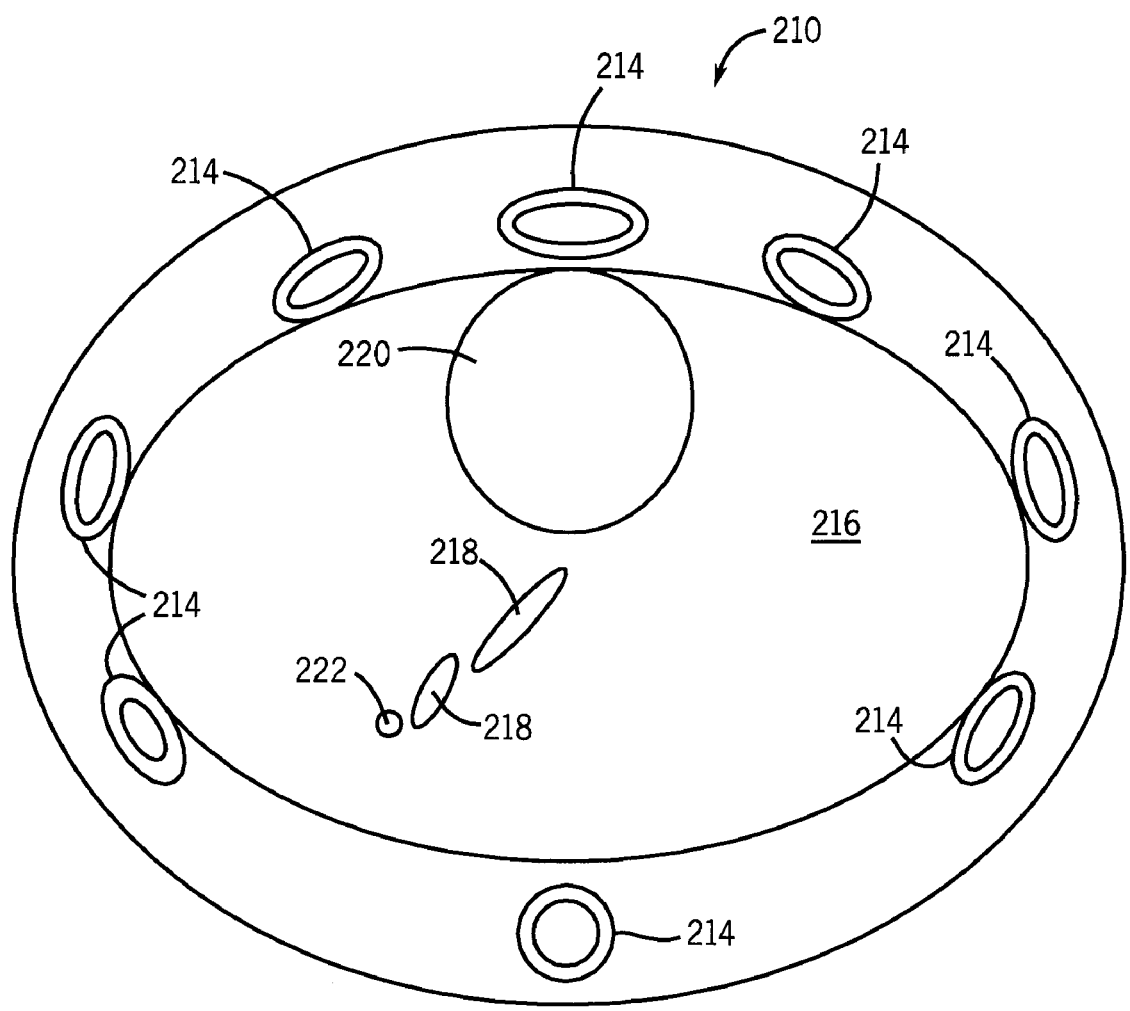
FIG. 8 is a schematic image of a phantom.

Referring now to FIG. 8, as an illustration of the present invention, a schematic diagram is shown of a phantom 210 for acquiring CT data for the embolism imaging process 120 of FIG. 7. Phantom 210 includes high density materials 214 which may include a sternum, ribs, or a spinal column. Phantom 210 includes lung tissue 216, a plurality of blood vessels 218 having contrast agent such as iodine therein, a heart 220, and a blood clot 222. Because of density differences and effective Z number differences of the materials within the phantom such as, for instance, iodine representing an intravenously administered contrast agent and water in normal tissue, a conventional CT image may not adequately distinguish between the features therein. A heart, blood vessel, and an embolism inherently contain water. A contrast agent, on the other hand, may reside only in a limited fashion within a patient during an imaging procedure.

For instance, as an intravenously administered contrast agent passes through blood vessels, the contrast agent may be present therein during the imaging process, but because the contrast agent has not yet passed to the heart through the bloodstream, the image of the heart does not contain the contrast agent. The embolism, on the other hand, though it inherently contains water, does not have contrast agent therein because the bloodstream, at the location of the embolism, is blocked and thereby not passing blood or contrast agent. Accordingly, it is contemplated that the embolism imaging process 120 of FIG. 8 may be used to distinguish between blood vessels and blood clot with use of a contrast agent and EDCT techniques disclosed herein.

Figure 9:
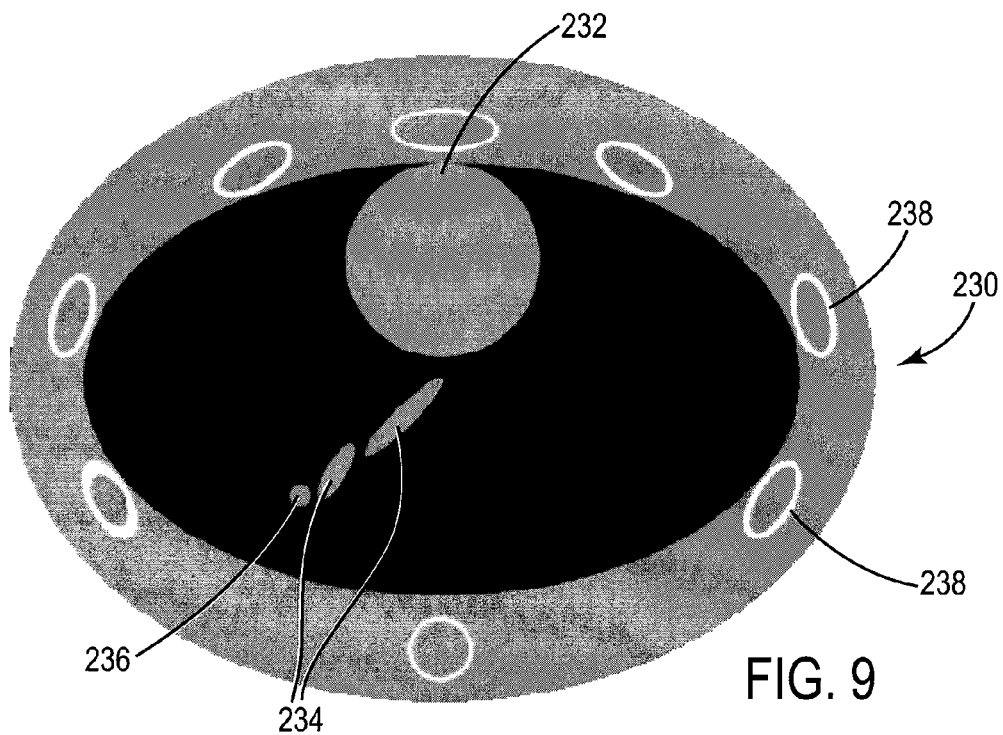
FIG. 9 represents images of the phantom represented by the schematic image of FIG. 8 obtained using energy discrimination, formed using a first basis material.
Figure 10:
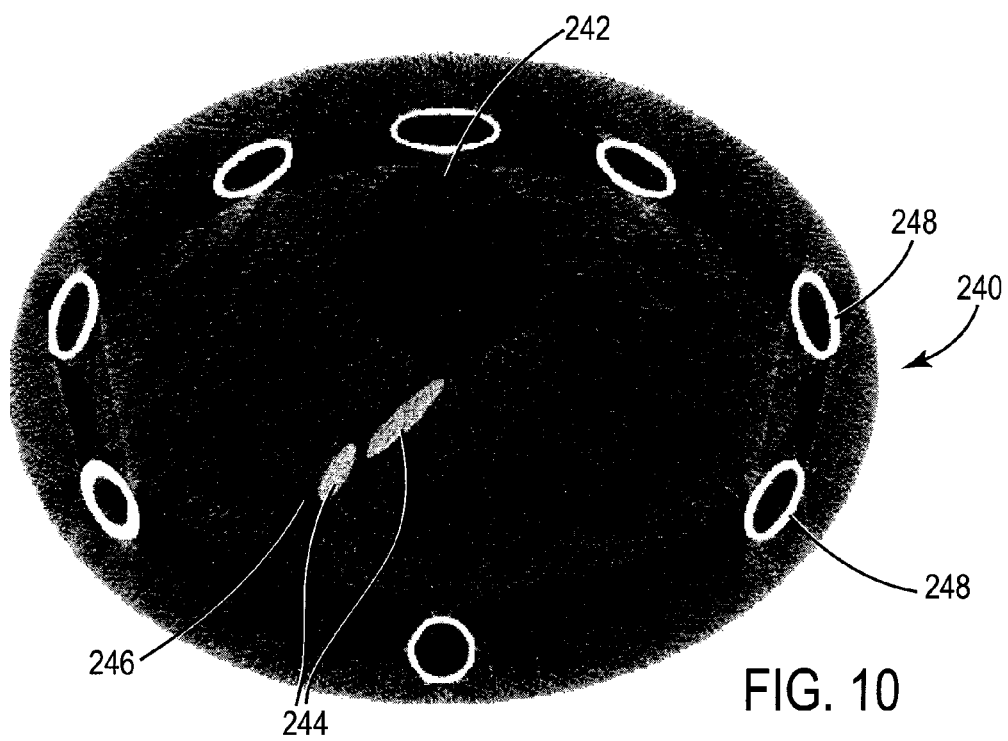
FIG. 10 represents images of the phantom represented by the schematic image of FIG. 8 obtained using energy discrimination, formed using a second basis material.

FIGS. 9 and 10 illustrate reconstructed images of the phantom 210 of FIG. 8 obtained using energy discrimination, based on numerical simulation. Image 230 of FIG. 9 is obtained by decomposing CT data acquired from phantom 210 of FIG. 8 into a first basis material, such as, for instance, water and reconstructing the decomposed first basis material into an image. Image 240 of FIG. 10 is obtained by decomposing CT data acquired from phantom 210 of FIG. 8 into a second basis material, using, for instance, a contrast agent such as iodine as the second basis material and reconstructing the decomposed second basis material into an image. Each pixel within image 230 contains a value for the amount of the first basis material in the pixel, and each pixel within image 240 contains a value for the amount of the second basis material in the pixel.

As shown in FIG. 9, heart 220 of FIG. 8 is visible at 232 due to the presence of water. On the other hand, as shown in FIG. 10, heart 220 of FIG. 8 at 242 is not visible because of a lack of contrast agent therein. As such, pixels of heart 220 contain an amount of water which effectively highlights the heart in image 230, but pixels of heart 220 contain very little contrast agent and are therefore difficult to distinguish in the second basis material image 240.

Similar to the heart 220 of FIG. 8, an embolism, such as blood clot 222 of FIG. 8, is visible at 236 in the water image 230. The visibility of the blood clot 222 at 236 in the water image 230 is due to the presence of water in blood clot 222. However, because the blood clot passes little or no contrast agent, there is therefore a minimal amount of image contrast agent present. Thus, the blood clot 222 is essentially invisible at 246 against the background in the image contrast image 240.

Contrary to the heart 220 and blood clot 222 of FIG. 8, blood vessels 218 are visible in both images 230 and 240 at 234 and 244, respectively, due to the presence of both water and image contrast agent therein. Similarly, high density materials 214 of FIG. 8 are visible in the water image 230 at 238 and in the image contrast agent image 240 at 248. However, unlike the blood vessels, high density materials 214 are visible in both images 230, 240 due to their very high density. This high density presents an illusion of having both high water density and high contrast agent density in the high density materials 214, though little or no water or contrast agent is present therein.

Figure 11:
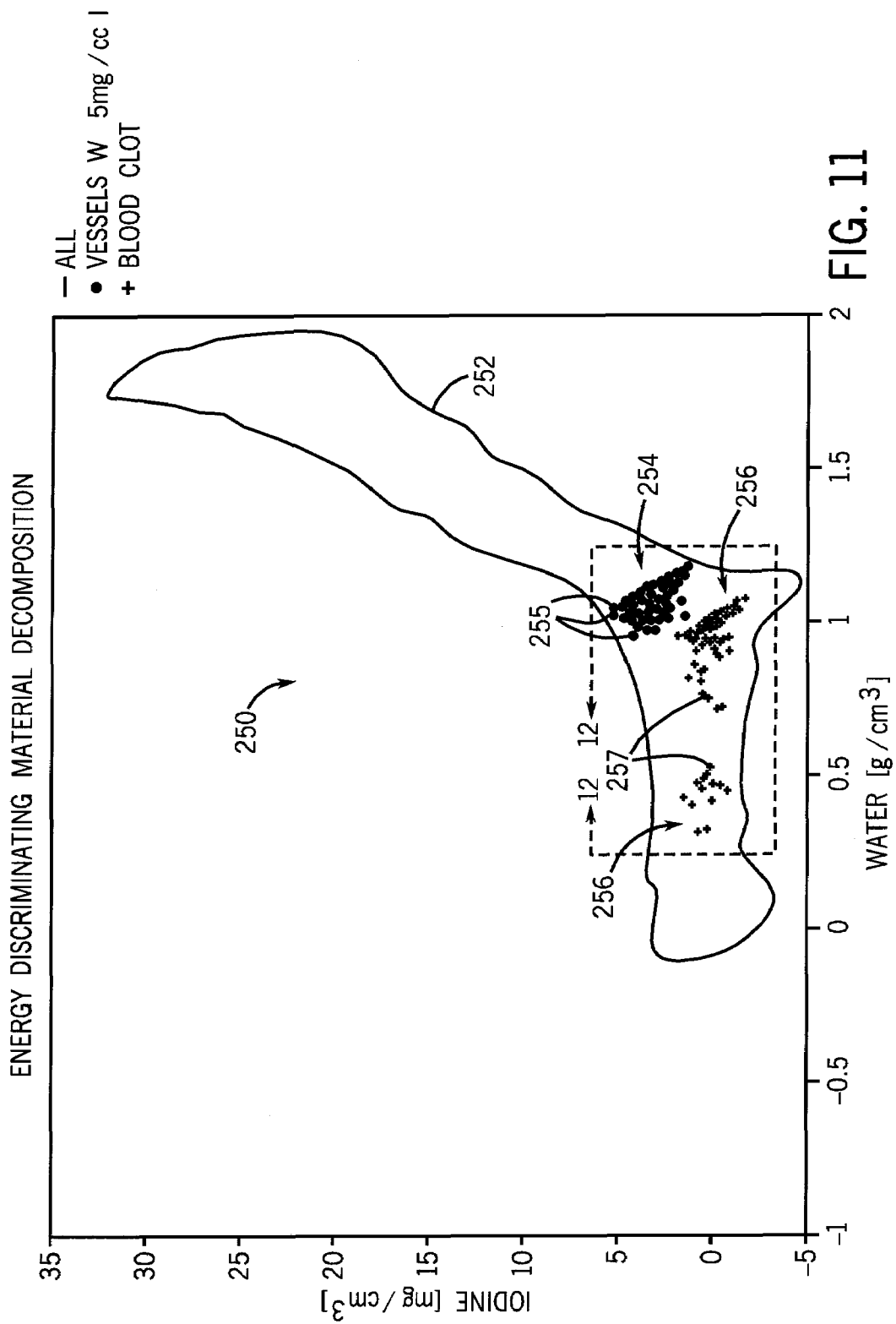
FIG. 11 illustrates a plot of pixels obtained from the decomposed images of FIGS. 9 and 10, each pixel classified and plotted according to basis material one and basis material two content.

FIG. 11 illustrates a material decomposition plot 250 of EDCT data acquired using phantom 210 of FIG. 8. The acquired data has been decomposed and classified as described above with regard to steps 112 through 136 of the embolism imaging process 120 of FIG. 7. Plot 250 shows an area 252 containing all pixels classified according to their iodine versus water content. For illustrative purposes, areas 254, 256 identify only pixels of blood vessels 218 and blood clot 222, respectively. One skilled in the art, however, would appreciate that area 252 contains information from all pixels.

As shown in FIG. 11, area 254 illustrates that pixels 255 from blood vessels 218 tend to form a group, and areas 256 illustrate that pixels 257 from blood clot 222 tend to form groups. As illustrated, areas 254 and 256 appear in distinct regions of plot 250. For reasons described above, blood vessel pixels 255 tend to have slightly higher water content than blood clot pixels 257, and blood vessel pixels 255 tend to have a higher contrast agent content than blood clot pixels 257.

Accordingly, because of the basis material decomposition of the image of the phantom, such information may be employed to identify pixels in a CT image reconstructed from EDCT data that will have a likelihood of being either of, for instance, a blood clot or a blood vessel. Likely blood vessel pixels and likely blood clot pixels may be displayed using separate colors, or may be otherwise identified in the reconstructed image to highlight their presence for a medical practitioner.

Figure 12:
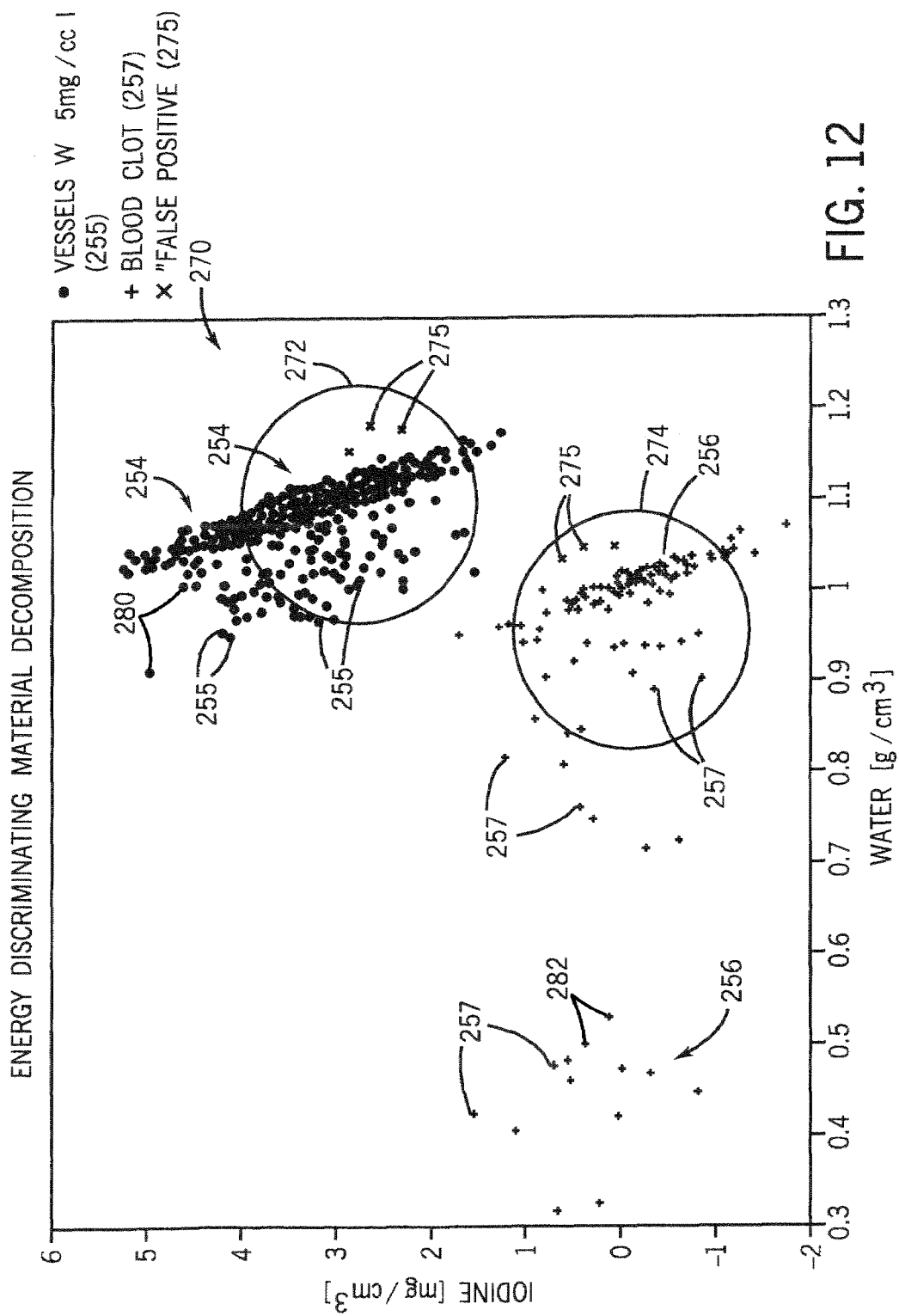
FIG. 12 illustrates the data of FIG. 12 showing only basis material one and basis material two pixels with reduced ranges on X and Y axes.

Referring now to FIG. 12, plot 270 illustrates a portion of plot 250 of FIG. 11 along line 12-12. It can be recognized that, due to the differing content of basis materials (in this case, water and iodine) in the two pixel types, the groupings of blood vessels 255 and blood clot pixels 257 lie in separate regions of the basis material plot 270. Such information may be used to identify which pixels of a reconstructed CT image are likely to be that of either a blood vessel or an embolism.

Accordingly, it is possible to know a priori which distinct regions of a plot of basis materials are likely to contain, for instance, a blood clot or a blood vessel, and automatically display them for a medical practitioner. That is, regions of a plot of basis materials may be identified that contain a predetermined basis material decomposition ratio of both materials. As an example, a first region 272, illustrated in this case as a circle, may be used to encompass a group of pixels that are in an area of the basis material decomposition plot 270 where the ratio of iodine to water in the region 272 falls within a threshold of a ratio of iodine to water of a predetermined blood vessel decomposition. As shown, first region 272 is centrally positioned at an iodine-to-water ratio of approximately 3:1.1 A second region 274, also illustrated as a circle, may be used to encompass a group of pixels that are in an area of the basis material decomposition plot 270 where the ratio of iodine to water in the region 274 falls within a threshold of a ratio of iodine to water of a predetermined blood clot decomposition. As shown, second region 274 is centrally positioned at an iodine-to-water ratio of approximately 0.95:0. It is contemplated that regions encompassing groups of pixels may have other shapes in addition to that shown in FIG. 12.

As can be seen, first region 272 contains many, but may not contain all, of the pixels of blood vessels. Likewise the second region 274 contains many, but may not contain all, of the pixels of a blood clot. Accordingly, regions 272, 274, being separate and distinct from one another, may be highlighted on for instance a conventional CT image as possible blood vessels or blood clots.

While identifying pixels that are likely to contain the item of interest, regions 272, 274 may also encompass pixels 275 that are not of interest to the practitioner for a given diagnosis. That is, while being encompassed in regions 272 or 274, pixels 275 do not correspond to either a blood vessel or a blood clot. Such pixels 275 falling within regions 272, 274 that are not pixels of blood vessels may be referred to as "false positives." Furthermore, regions 272, 274 may not encompass all blood vessel pixels 255 or blood clot pixels 257, respectively. As an example, blood vessel pixels 280 and blood clot pixels 282 that fall outside regions 272, 274, respectively result in what may be referred to as "false negatives."

Figure 13:
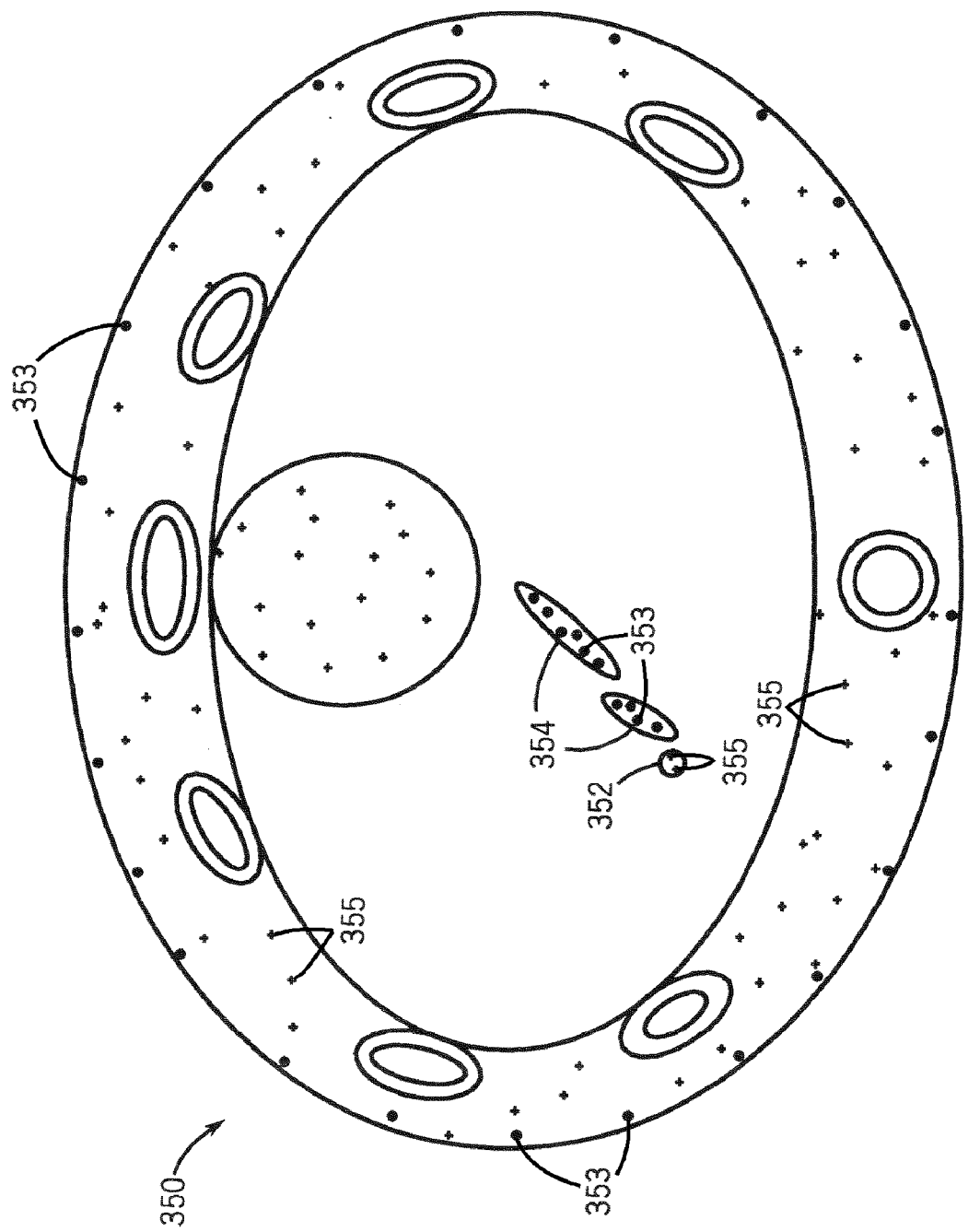
FIG. 13 is an illustration of an image obtained according to an embodiment of the present invention.

FIG. 13 shows a schematic diagram of an image 350 having pixels identified thereon according to an embodiment of the present invention. A plurality of possible blood vessel pixels 353 highlighted on image 350 were identified as being within region 272 of FIG. 12. Similarly, a plurality of possible blood clot pixels 355 highlighted on image 350 were identified as being within region 274 of FIG. 12. In a preferred embodiment, the possible blood vessel pixels 353 are highlighted with a first color, symbol, or other identifier, and the possible blood clot pixels 355 are highlighted with a second color, symbol, or other identifier. It is contemplated, however, that pixels 353, 355 maybe identified with other types of identification.

As discussed above with respect to FIG. 12, regions 272, 274 may contain false positives that are highlighted on image 350 as possible blood vessel pixels 353 or possible blood clot pixels 355. As shown in FIG. 13, highlighted false positives are shown in areas of image 350 where no blood vessel or blood clot exists. Typically, the highlighted false positives will be randomly dispersed throughout image 350, and, though they will show as a color or other identifier, they will tend not to be bunched together. On the other hand, highlighted pixels of true blood vessels or blood clots will tend to be bunched together. Accordingly, the eye of a medical practitioner may be drawn only to the bunched and highlighted pixels as in, for instance, groups 352 and 354 where an actual blood clot and actual blood vessel, respectively, may be.

In addition to highlighting false positives, FIG. 13 shows that pixels corresponding to false negatives have not been highlighted. That is, a false negative pixel of, for instance, a blood vessel will show as a conventional image pixel and will be positioned in the image at 354, but it will not be colored or highlighted as a blood vessel pixel. Similarly, a false negative pixel of, for instance, a blood clot will, as well, show in the region of the blood clot 352 as a conventional image pixel, but it will not be colored or highlighted as a blood clot pixel. However, because the disclosed technique is designed to capture a majority of the blood clot and blood vessel pixels, the number of highlighted false positive pixels and non-highlighted false negative pixels should not distract the practitioner from the concentration of colored pixels highlighting, for instance, true blood clot and blood vessel pixels.

Accordingly, a conventional CT image having highlighted thereon a possible blood clot, thrombus, or embolism with a color or other identifier as well as a possible blood vessel with another color or other identifier allows a medical practitioner or radiologist to more quickly and efficiently diagnose an embolism or thrombus. The possible blood clot, thrombus, or embolism may be automatically displayed on, for instance, a conventional CT image. The practitioner is thus enabled to quickly and efficiently distinguish a blood clot from a blood vessel or other part of the anatomy.

Therefore, an embodiment of the present invention includes an imaging scanner. The imaging scanner includes a radiation source, a radiation detector, and a computer programmed to decompose CT data acquired by the radiation detector into a set of pixels, each pixel having at least a first basis material content and a second basis material content. The computer is further programmed to identify a first subset of the set of pixels as a possible embolism, based on the content of the first basis material and the content of the second basis material.

According to another embodiment of the present invention, a method of CT imaging includes a method of CT imaging includes acquiring energy sensitive CT data from an ROI of a subject, classifying the acquired energy sensitive CT data as pixels having content from a first basis material and content from a second basis material, and determining a first set of the classified pixels as a possible blood clot.

Yet another embodiment of the present invention further includes a computer program stored on a computer readable storage medium. The computer program includes receiving energy sensitive CT data acquired from a subject decompose the energy sensitive CT data into at least two basis material datasets, assigning a first basis material content and a second basis material content to each pixel of an image, identifying a first set of pixels in the image as possible blood clot based on the first and second basis material content, and reconstructing a conventional CT image with the first set of pixels highlighted.

The present invention has been described in terms of the preferred embodiment, and it is recognized that equivalents, alternatives, and modifications, aside from those expressly stated, are possible and within the scope of the appending claims.

What is claimed is:

1. An imaging scanner comprising:
   a radiation source;
   a radiation detector; and
   a computer programmed to:
      decompose CT data acquired by the radiation detector into a set of pixels, each pixel having at least a first basis material content and a second basis material content;
      identify a first subset of the set of pixels as a possible embolism, based on a first predetermined content of both the first basis material and the second basis material; and
      generate a conventional CT image using the CT data, the conventional CT image having the first subset of pixels highlighted.

2. The imaging scanner of claim 1 wherein the computer is further programmed to identify a second subset of the set of pixels as a possible blood vessel based on a second predetermined content of both the first basis material and the second basis material.

3. The imaging scanner of claim 2 wherein the computer is further programmed to highlight the second subset of pixels in the conventional CT image.

4. The imaging scanner of claim 3 wherein the computer is further programmed to automatically identify one of the first and second subsets of pixels in the conventional CT image.

5. The imaging scanner of claim 2 wherein the computer is further programmed to identify the first subset of pixels as a first color and the second subset of pixels as a second color.

6. The imaging scanner of claim 1 wherein the first basis material content is water and the second basis material content is a contrast agent.

7. The imaging scanner of claim 6 wherein the contrast agent is iodine.

8. The imaging scanner of claim 6 wherein the contrast agent is perfused in a scanning subject.

9. The imaging scanner of claim 1 wherein the embolism is one of a pulmonary embolism and a deep venous thrombosis in the leg.

10. A method of CT imaging comprising the steps of:
    acquiring energy sensitive CT data from an ROI of a subject;
    classifying the acquired energy sensitive CT data as pixels having content from a first basis material and content from a second basis material; and
    determining a first set of the classified pixels as a possible blood clot based on a first preset content of both the first basis material and the second basis material.

11. The method of claim 10 further comprising:
    determining a second set of the classified pixels as a possible blood vessel based on a second preset content of the first basis material and the second basis material.

12. The method of claim 11 wherein one of the steps of determining a first set and determining a second set is automatically performed.

13. The method of claim 11 further comprising:
    overlaying the first set and the second set of the classified pixels on a CT image.

14. The method of claim 13 wherein overlaying the first set and the second set of classified pixels comprises overlaying the first set with a first color and the second set with a second color.

15. The method of claim 10 wherein the image is a conventional CT image.

16. The method of claim 10 further comprising injecting an imaging contrast material capable of perfusion into the subject.

17. The method of claim 16 wherein the second basis material is the same material as the imaging contrast material.

18. The method of claim 16 wherein injecting comprises injecting iodine into the subject.

19. The method of claim 10 wherein the first basis material is water.

20. A computer readable storage medium having a computer program stored thereon and representing a set of instructions that when executed by a computer causes the computer to:
    determine, prior to acquiring CT data, a first basis material content and a second basis material content likely to indicate presence of a blood clot in a CT image constructed from energy sensitive CT data;
    receive energy sensitive CT data acquired from a subject;
    decompose the energy sensitive CT data into two basis material datasets;
    assign a first basis material content and a second basis material content to each pixel of an image;
    identify a first set of pixels in the image as possible blood clot having the determined first and second basis material content that indicate presence of a blood clot; and
    reconstruct a conventional CT image with the first set of pixels highlighted.

21. The computer readable storage medium of claim 20 wherein at least one of the steps is automatically performed.

22. The computer readable storage medium of claim 20 wherein the computer is further caused to highlight the first set of pixels using a first color.

23. The computer readable storage medium of claim 22 wherein the computer is further caused to:
- determine, prior to acquiring CT data, a first basis material content and a second basis material content likely to indicate presence of a blood vessel in a CT image constructed from energy sensitive CT data; and
- identify a second set of pixels in the image as possible blood vessel having the determined first and second basis material content that indicates presence of a blood vessel.

24. The computer readable storage medium of claim 23 wherein the computer is further caused to highlight the second set of pixels on the reconstructed image.

25. The computer readable storage medium of claim 24 wherein the computer is further caused to highlight the second set of pixels using a second color.

26. The computer readable storage medium of claim 20 wherein the first basis material content is water and wherein the second basis material content is a contrast agent.

27. The computer readable storage medium of claim 26 wherein the contrast agent is iodine.

* * * * *